(12) United States Patent
Minocha et al.

(10) Patent No.: US 12,653,708 B2
(45) Date of Patent: Jun. 16, 2026

(54) STENT SYSTEM FOR TREATING DIFFUSED LESIONS IN BIFURCATED ARTERIES

(71) Applicant: MERIL LIFE SCIENCES PVT LTD., Vapi (IN)

(72) Inventors: Pramod Kumar Minocha, Vapi (IN); Deveshkumar Mahendralal Kothwala, Surat (IN); Harshad Amrutlal Parmar, Vapi (IN)

(73) Assignee: MERIL LIFE SCIENCES PVT LTD., Vapi (IN)

( * ) Notice: Subject to any disclaimer, the term of this patent is extended or adjusted under 35 U.S.C. 154(b) by 1010 days.

(21) Appl. No.: 17/790,199

(22) PCT Filed: Feb. 28, 2020

(86) PCT No.: PCT/IN2020/050183
§ 371 (c)(1),
(2) Date: Jun. 30, 2022

(87) PCT Pub. No.: WO2021/140518
PCT Pub. Date: Jul. 15, 2021

(65) Prior Publication Data
US 2022/0354676 A1 Nov. 10, 2022

(30) Foreign Application Priority Data
Jan. 10, 2020 (IN) .............................. 202021001212

(51) Int. Cl.
A61F 2/954 (2013.01)
A61F 2/91 (2013.01)
A61F 2/958 (2013.01)

(52) U.S. Cl.
CPC ................ *A61F 2/954* (2013.01); *A61F 2/91* (2013.01); *A61F 2/958* (2013.01); *A61F 2250/0067* (2013.01)

(58) Field of Classification Search
CPC .... A61F 2/82; A61F 2/95; A61F 2/954; A61F 2/958; A61M 25/10; A61M 2025/1068
See application file for complete search history.

(56) References Cited

U.S. PATENT DOCUMENTS 6,409,741 B1 * 6/2002 Crocker .................... A61F 2/86
606/192

* cited by examiner

*Primary Examiner* — William H Matthews
(74) *Attorney, Agent, or Firm* — KNH LLP

(57) ABSTRACT

A stent system is disclosed. The stent system includes a balloon catheter having a balloon with a proximal zone, a transition zone and a distal zone including progressively decreasing diameters respectively. The stent of a pre-defined length includes a main branch segment, a transition segment and a side branch segment. The stent includes an expanded state and a crimped state. The stent is mounted over the balloon in the crimped state such that the main branch segment is mounted over the proximal zone, the transition segment is mounted over the transition zone and the side branch segment is mounted over the distal zone. In expanded state, the main branch segment, the transition segment and the side branch segment of the stent correspond to the respective zones of the balloon. The transition segment includes plural rows of elongated members connected to each other.

10 Claims, 7 Drawing Sheets

300

STENT SYSTEM FOR TREATING DIFFUSED LESIONS IN BIFURCATED ARTERIES

FIELD OF INVENTION

The present invention relates to a medical device. More specifically, the present invention relates to a stent system for treating diffused lesions in bifurcated coronary arteries.

BACKGROUND

Coronary artery disease (CAD) is the most often found cardiovascular disease all around the globe. CAD tends to develop when cholesterol builds up on the artery walls of a patient, thereby creating plaques. These plaques render the arteries narrow, thus, reducing blood flow to the heart.

A lot of treatment strategies for curing the said disease have been suggested/devised however, treating complex bifurcated lesions in coronary arteries still remains challenging owing to different diameter and length of the lesions. A coronary bifurcation lesion occurs at or near a division of a major coronary artery. These cardiovascular diseases are one of the most life-threatening diseases leading to higher mortality rates.

Owing to complexity in the structure of the bifurcated coronary artery, the conventional stents may not be ideal for treating bifurcated lesions and may be limited by several factors including side branch ostial gaps, main branch stent overlap, stent distortion, and procedural complications such as guide wire entanglement etc.

Various other methods have been utilized to treat bifurcated lesions such as a T-stent approach. In this method, a surgeon deploys a stent in the side branch followed by deployment of a stent in the main branch. This method is limited by anatomic variation (angle between the main branch and the side branch) and/or inaccuracy in stent positioning, which may cause inadequate coverage of the side branch.

Another method for treatment of the bifurcated lesions may include crush approach. In this method, the side branch of the bifurcated artery is deployed with the stent with some portion of the stent being deployed in both the main and side branch vessels. The main branch of the artery is then deployed with another stent across the origin of the side branch. This may result in crushing a portion of the side branch stent against the main branch and/or may lead to difficulty in re-entering the side branch stent after crushing with main branch. Also, there may be a possibility of false positioning of the stent in this method.

Therefore, side branch stent has been developed to treat lesions in the bifurcated artery of a patient. However, the conventional side branch stent may pose certain limitations, such as Insufficient length of side branch segment that may not cover the length of diffused side branch lesion, overlapping of the main branch stent, migration of the stent due to ostial gaps and/or higher strut thickness etc.

Therefore, there exists a need for an improved side branch stent that can overcome limitations offered by the conventional ones.

SUMMARY

The present invention discloses a stent system. The stent system includes a balloon catheter having a balloon with a proximal zone, a transition zone and a distal zone including progressively decreasing diameters respectively. The stent of a pre-defined length includes a main branch segment, a transition segment and a side branch segment. The stent includes an expanded state and a crimped state. The stent is mounted over the balloon in the crimped state such that the main branch segment is mounted over the proximal zone, the transition segment is mounted over the transition zone and the side branch segment is mounted over the distal zone. In expanded state, the main branch segment, the transition segment (and the side branch segment of the stent correspond to the respective zones of the balloon. The transition segment includes plural rows of elongated members connected to each other.

BRIEF DESCRIPTION OF DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the disclosure is not limited to specific methods and instrumentalities disclosed herein. Moreover, those in the art will understand that the drawings are not to scale.

DETAILED DESCRIPTION OF THE DRAWINGS

Figure 1:
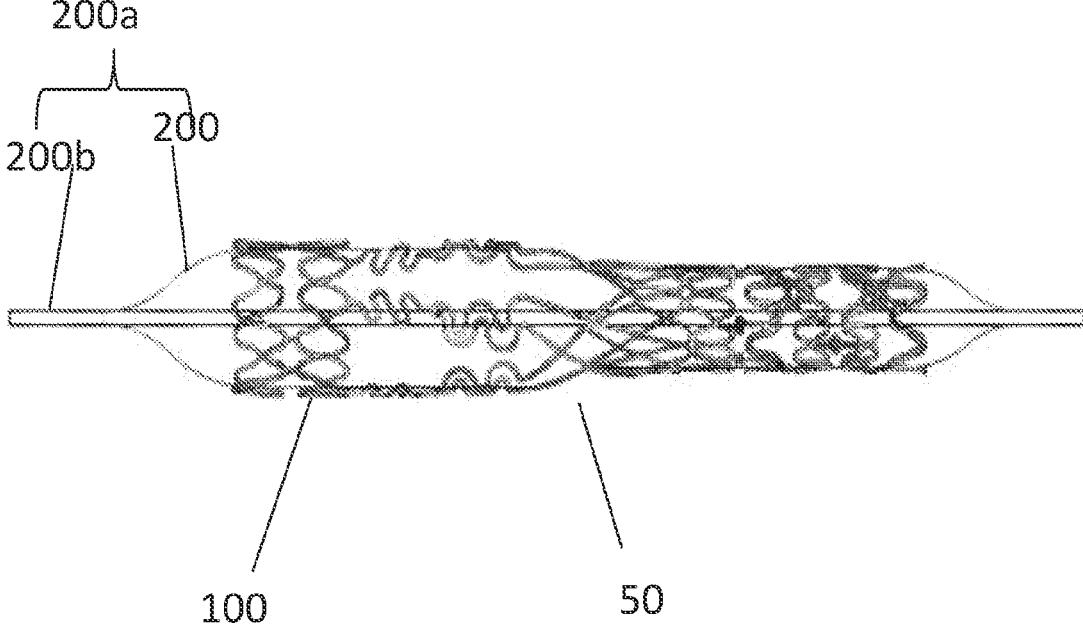
FIG. 1 represents a stent system in accordance with an embodiment of the present invention.

Prior to describing the invention in detail, definitions of certain words or phrases used throughout this patent document will be defined: the terms "include" and "comprise", as well as derivatives thereof, mean inclusion without limitation; the term "or" is inclusive, meaning and/or; the phrases "coupled with" and "associated therewith", as well as derivatives thereof, may mean to include, be included within, interconnect with, contain, be contained within, connect to or with, couple to or with, be communicable with, cooperate with, interleave, juxtapose, be proximate to, be bound to or with, have a property of, or the like; Definitions of certain words and phrases are provided throughout this patent document, and those of ordinary skill in the art will understand that such definitions apply in many, if not most, instances to prior as well as future uses of such defined words and phrases.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments. These features and advantages of the embodiments will become more fully apparent from the following description and appended claims, or may be learned by the practice of embodiments as set forth hereinafter.

It should be noted that 'stent' and 'coronary stent' in the following description are interchangeably used to confer the same meaning. Likewise, 'delivery catheter', 'balloon catheter' and 'catheter' have been interchangeably used to confer the same meaning. Also, 'biodegradable' and 'bioresorbable' have been interchangeably used to confer the same meaning. It should be further noted that the term 'diameter' in the following description corresponds to outer diameter until and unless specified otherwise.

In accordance with the present disclosure, a coronary stent mounted over an expandable member of a delivery catheter (collectively referred to as a 'stent system') is disclosed. The coronary stent of the present invention is deployed with the help of the balloon catheter at an implantation site. The implantation site in the present invention corresponds to for example, a long and diffused side branch lesion in a bifurcated coronary artery anatomy of a patient. In an embodiment, the stent of the present invention is deployed within a bifurcated body lesion and more particularly, at an ostial opening from a main body lesion to a branch body lesion. The present invention may also be used for other implantation sites such as carotid as well as peripheral vasculature.

The stent of the present invention includes a hybrid design having a plurality of segments. In an embodiment, the stent includes three segments i.e. a main branch segment, a transition segment and a side branch segment. The main branch segment is deployed at the main body lesion while the side branch segment is deployed at the branch body lesion of the bifurcated body lesion. The side branch segment of the stent has a tapered profile and includes a length of ranging between 03 mm and 25 mm. Owing to the longer length and smaller diameter of the side branch segment, the stent of the present invention renders better conformability to the anatomy of the implantation site as compared to the conventional stents.

Further, the struts of the stent are ultra-thin which result in minimum injury post implantation of the stent at the implantation site and also minimize the possibility of initial restenosis.

The balloon catheter may have a stepped expandable member, say balloon, to suit the bifurcated coronary artery anatomy. The use of the stepped balloon allows even expansion of the stent. The stent hence, mimics the natural anatomy of the bifurcated coronary artery, thus overcoming the challenges associated with the conventional systems due to bifurcation of the coronary arteries.

Now referring to figures, FIG. 1 shows a stent system 50 of the present invention. The stent system 50 is employed to be used for treating multiple blockages of the bifurcated coronary artery and the side branch lesions as well as the long length lesions therein.

The crimp profile of the stent system 50 may range from 0.95 mm to 1.37 mm. In an embodiment, the crimp profile of the stent system 50 is 1.10 mm. The stent system 50 includes a guide-catheter compatibility as low as 6 F which is similar to any shorter conventional cylindrical stents. Thus, the stent system 50 provides superior conformability in the side branch coronary artery as compared to multiple overlapping stents. The stent system 50 allows an interventional cardiologist to safely expand the stenosed segment to the diameter of the artery.

As depicted in FIG. 1, the stent system 50 includes a stent 100 mounted over a balloon catheter 200a. The balloon catheter 200a in turn includes a shaft 200b and a balloon 200. Further, the balloon catheter 200a may include a plurality of radio opaque markers (not shown). The radio opaque markers may be mounted on an inner lumen of the balloon catheter 200a for better visibility during radio graphic examination.

The shaft 200b of the balloon catheter 200a may be structurally and functionally equivalent to any conventionally known/used shaft of a balloon catheter.

Figure 4:
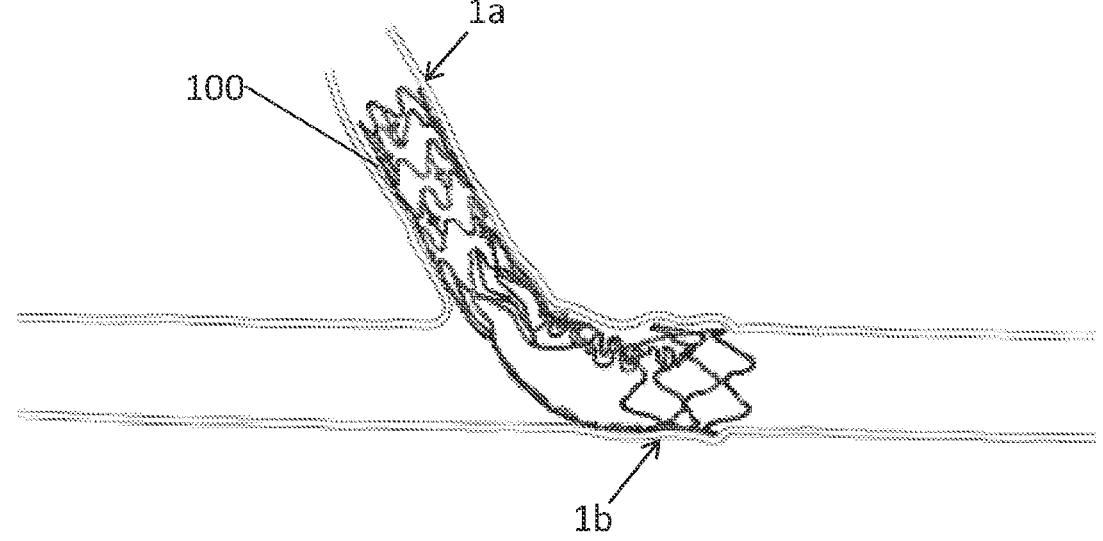
FIG. 4 represents a stepped stent implanted at the treatment site in accordance with an embodiment of the present invention.

The stent 100 of the present invention provides complete coverage of the wall of a side branch lumen 1a as depicted in FIG. 4.

The stent 100 of the present invention may be made of any metallic material, without limitation, stainless steel (316LVM), cobalt chromium alloy (L605), etc. In an embodiment, the stent 100 is fabricated from a cobalt-chromium alloy which is widely used for manufacturing implants in the medical industry due to its shape memory and bio-compatibility property. Further, the use of cobalt-chromium alloy offers various advantages over other materials which include, without limitation, kink resistance, crush resistance, flexibility and high amount of recoverable deformation. The process of manufacturing a metallic stent 100 is provided in FIG. 6.

Alternately, the stent 100 may be fabricated from conventional bioresorbable polymers or biodegradable metals known in the art. The bioresorbable polymers may be selected from, without limitation, poly-L-lactide, poly-DL-lactide, poly-L-lactide-co-glycolide, poly-L-lactide-co-caprolactone or combination thereof. The biodegradable metals used for the present invention may be magnesium, iron or alloys thereof.

The stent 100 of the present invention includes features such as flexibility, vessel wall coverage, and deployment accuracy to ensure lesion coverage, etc.

The stent 100 is adapted for placement at an ostium opening from a main branch to a side branch of the coronary artery. The stent 100 includes a proximal end 101 and a distal end 103. The distance between the proximal end 101 and the distal end 103 define a length (L) of the stent 100. The length (L) of the stent 100 may be in a range of to 16 mm to 29 mm. In an embodiment, the length of the stent 100 is 24 mm.

The stent 100 includes a main branch segment 10, a transition segment 20 and a side branch segment 30 between the proximal end 101 and the distal end 103.

The main branch segment 10 is disposed towards the proximal end 101 of the stent 100. In an embodiment, the main branch segment 10 is disposed at a main branch 1*b* post implantation of the stent 100 as shown in FIG. 4.

The main branch segment 10 includes a proximal end 10*a* and a distal end 10*b*. The distance between the proximal end 10*a* and the distal end 10*b* of the main branch segment 10 defines a length of the main branch segment 10. The main branch segment 10 may include a predefined length (L1). The predefined length (L1) of the main branch segment 10 of the stent 100 may be in a range of 4.5 mm to 7.00 mm. In an embodiment, the predefined length (L1) of the main branch segment 10 of the stent 100 is 6.6 mm.

Further, the main branch segment 10 may include an outer diameter D1. The outer diameter D1 of the main branch segment 10 is larger in comparison to the side branch segment 30 to match the dimension of the main branch lesion in order to avoid the movement of the stent in the lesion post implantation. The diameter D1 may be in a range of 2.00 mm to 5.00 mm. In an embodiment, the diameter D1 of the main branch segment 10 is 3.00 mm.

The main branch segment 10 includes a plurality of struts members 11. The thickness of the strut members 11 may be in a range of 40 micron to 100 microns. In an embodiment, the thickness of the struts members 11 may be 65 microns.

The strut members 11 may be interconnected with each other to form at least one row of closed cells 12*a*, 12*b*. In an embodiment, the main branch segment 10 includes two rows of closed cells 12*a* and 12*b* (FIG. 2) at the proximal end 10*a* of the main branch segment 10.

Further, the main branch segment 10 may include a plurality of connecters to connect the two rows of closed cells (12*a*, 12*b*) to the transition segment 20 of the stent 100. In an embodiment, the main branch segment 10 includes two rows of connectors, a row of first connectors 13*a* and a row of second connectors 13*b*.

The connectors (13*a*, 13*b*) may be provided in any shape such as without limitation, spiral, s-shaped, N-shaped, v-shaped etc. In an embodiment, the connectors (13*a*, 13*b*) are provided in s-shaped. In an embodiment, the first connectors 13*a* may be a S link slightly titled in a predefined direction and the second connectors 13*b* may be a double S link connecting the main branch segment 10 with the transition segment 20. The s-shaped links ay provide excellent flexibility, allows for morphology mediated expansion and adequate conformability to the main branch segment 10 of the stent 100.

In an embodiment, valleys of the lower row of closed cells 12*b* are connected to the first connector 13*a* and a lower end of the first connector 13*a* are connected to the second connector 13*b*.

Figure 2:
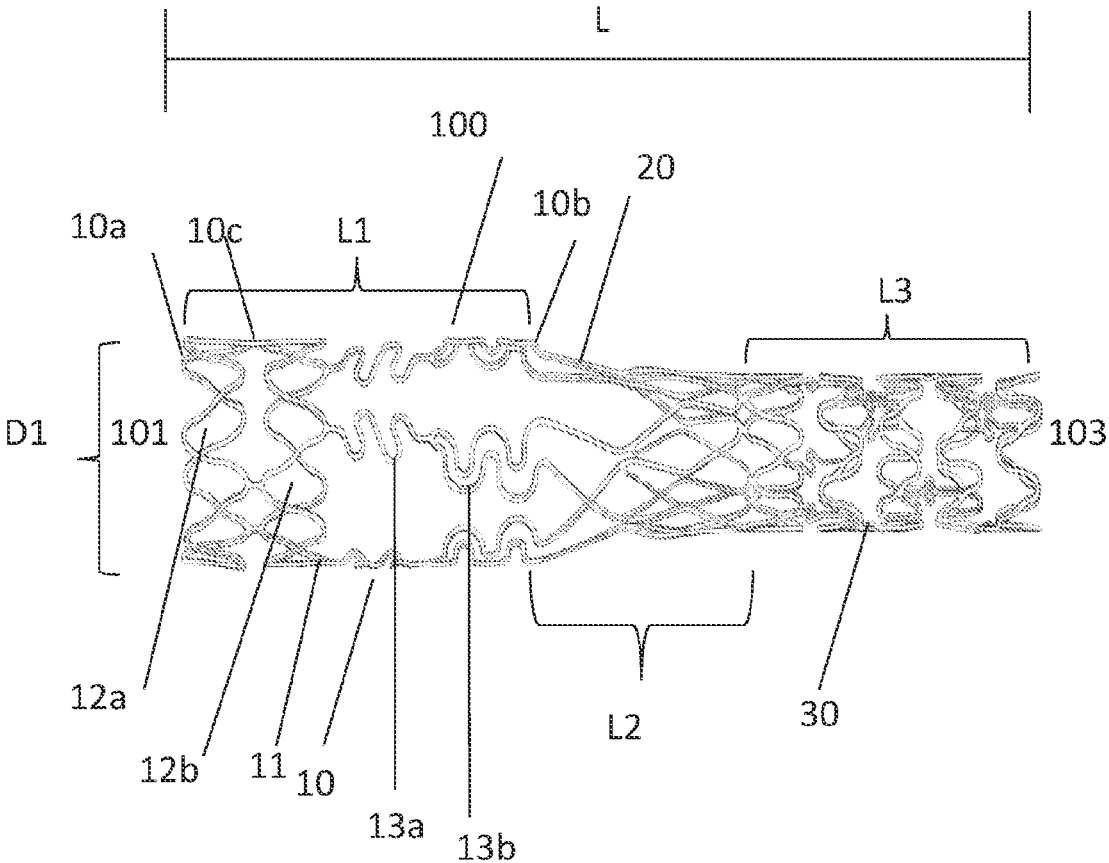
FIG. 2 represents a perspective view of a stent in accordance with an embodiment of the present invention.

Further, the transition segment 20 of the stent 100 is adapted to support the ostium 43 (depicted in FIG. 4) when deployed. The transition segment 20 is able to provide a greater degree of scaffolding in the area of the ostium and/or provides enhanced ability of the stent 100 to effectively maintain the ostium open after implantation. The transition segment 20 may include a plurality of elongated members 21. The elongated members 21 may be connected to the second connector 13*b* of the main branch segment 10. In an embodiment, the elongated members 21 extends from the second connector 13*b* of the main branch segment 10 as depicted in FIG. 2. In an embodiment, the transition segment 20 of the stent 100 permits optional placement of another stent within the main branch of the artery using the conventional technique.

The transition segment 20 may include a length (L2) and an outer diameter (D2). The length of transition segment 20 may be in a range of 3.0 mm to 6.0 mm. In an embodiment, the length of the transition segment 20 is 4.5 mm. In another embodiment, the outer diameter (D2) of the transition segment 201*s* tapered. In an embodiment, the outer diameter (D2) of the transition segment 20 gradually tapers from the distal end 10*b* of main branch segment 10 to a proximal end 32 of the side branch segment 30 as depicted in FIG. 2. The outer diameter of transition segment may depend upon the outer diameter of main branch segment 10 and side branch segment 30.

In an embodiment, the stent 100 includes the side branch segment 30 towards the distal end 103 of the stent 100. The side branch segment 30 is adapted to support the long-diffused lesions of the side branch of the artery. The side branch segment 30 includes the proximal end 32 and a distal end 34. The side branch segment 30 may include a second predefined length (L3) between the proximal end 32 and the distal end 34. The predefined length (L3) of the side branch segment 30 of the stent 100 may be in a range of 03 mm to 25 mm, preferably 06 mm to 20 mm. In an embodiment, the predefined length (L3) of the side branch segment 30 of the stent 100 is 6.6 mm to 18.30 mm. The side branch segment 30 is made longer to enable to cover optimal length of the side branch lesions and/or to provide enhanced ability of the stent 100 to effectively maintain the ostium open after implantation. Further, longer side branch segment 30 of the stent 100 may prevent restenosis after deployment and/or damage to the coronary artery.

Further, the side branch segment 30 may include an outer diameter D3. The outer dimeter D3 of the side branch segment 30 is made smaller than the outer diameter D1 of the main branch segment 10. The smaller diameter of the side branch segment 30 enables optimal fixation of the side branch segment 30 with the diffused tapered lesion. The diameter D3 of the side branch segment 30 may be in a range of 2.00 mm to 4.00 mm. In an embodiment, the diameter D3 of the side branch segment 30 is 2.50 mm.

Figure 2A:
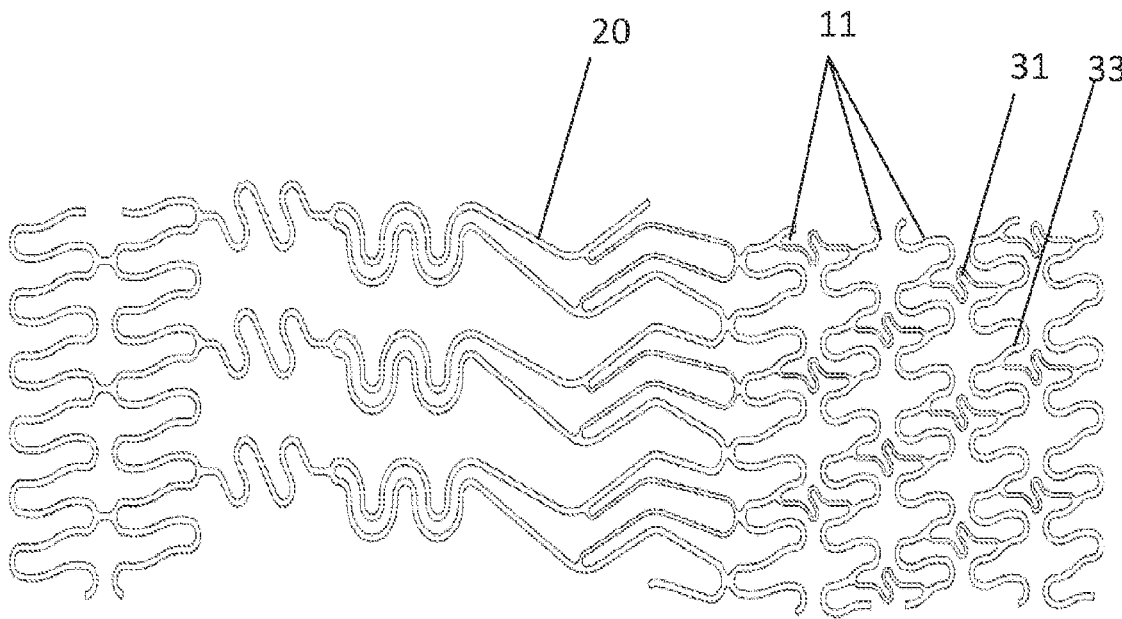
FIG. 2*a* represents an expanded view of the stent in accordance with an embodiment of the present invention.

As shown in FIG. 2*a*, the side branch segment 30 may be connected to an end of the transition segment 20. The side branch segment 30 of the stent 100 includes a plurality of circumferential rows of strut members 11 which are interconnected with at least one non-linear S link 31 and at least one Y connector 33. Though the description elaborates the use of non-linear S links 31 and Y connectors 33 in particular, other types of links and connectors may also be utilized for interconnection of rows of the present invention. The use of such links and connectors provide high flexibility to the side branch segment 30 with adequate side branch access and uniform radial strength.

Each circumferential row of strut members 11 includes peaks and valleys and forms a crown. The numbers of crowns in the side branch segment 30 may ranges from 4 to 12 depending upon the length (L3) of the side branch segment 30.

Figure 2B:
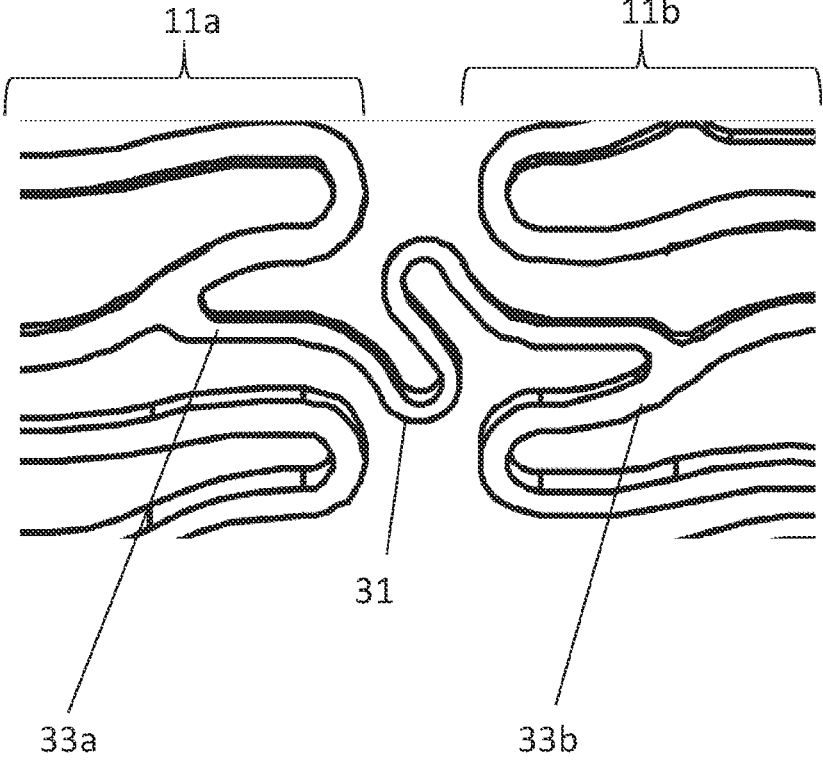
FIG. 2*b* represents a side branch segment of the stent in accordance with an embodiment of the present invention.

In an embodiment, S links 31 are used to form a linkage between two adjacently placed circumferential rows of strut members 11 as clearly depicted in FIG. 2b. Two Y connectors 33a, 33b connect the ends of an S link 31 with a first circumferential row of struts 11a and as second circumferential row of struts 11b at a predefined position as evident from FIG. 2b. The aforesaid structure of the stent 100 including main branch segment 10 and side branch segment 30 separated by a tapered transition segment constitutes hybrid structure of the stent 100. The said hybrid design of the stent 100 allows morphology mediated expansion of the stent 100 at the treatment site. Further, the said structure of the stent 100 provides enough strength and flexibility to the stent 100 at the main branch, passage in bifurcation point as well as diffused lesions in the side branch segment 30 of the artery. Further, owing to the hybrid design of the stent 100, the expansion of the stent 100 does not include dog-boning which is a common effect in conventional stent designs. Also, such a hybrid design ensures minimal edge injury during the deployment and implantation of the stent 100.

The stent 100 has ultra-thin struts members 11 for providing enough flexibility to the stent 100 without compromising radial strength of the stent 100. The radial strength of the stent 100 may ranges from 300 mmHg to 600 mmHg, preferably 350 mmHg to 550 mmHg. Further, owing to hybrid design of the stent 100, testing of the stent 100 demonstrates uniform radial strength of across the entire length of stent 100 and recoil less than 5% resulting in only 1% foreshortening of the stent 100. Moreover, the stent 100 has great kinking resistance and/or has kink radius <=15 mm.

The stent 100 may be coated with an anti-proliferative drug or a formulation of anti-proliferative drug as well as a polymer (or multiple polymers) as elaborated below.

The bench testing of stent 100 of the present invention post coating demonstrates a uniform radial strength across the entire length of the stent 100. Further, the stent 100 has a recoil less than 4% and foreshortening within ±1%. Moreover, the stent 100 was found to be free from cracks, scratches and change in stent geometry when expanded at rated burst pressure.

The stent 100 may be coated with an anti-proliferative drug or a formulation of anti-proliferative drug as well as a polymer (or multiple polymers) as elaborated below.

The stent 100 as described above is crimped over the balloon 200 (depicted in FIG. 3) and deployed within the patient's body. Once, the stent system 50 (stent along with the balloon) approaches the implantation site, the balloon 200 is inflated and the stent 100 is expanded to achieve a stepped profile. FIG. 4 illustrates the stent 100 implanted within the implantation site i.e bifurcated coronary artery.

Figure 3:
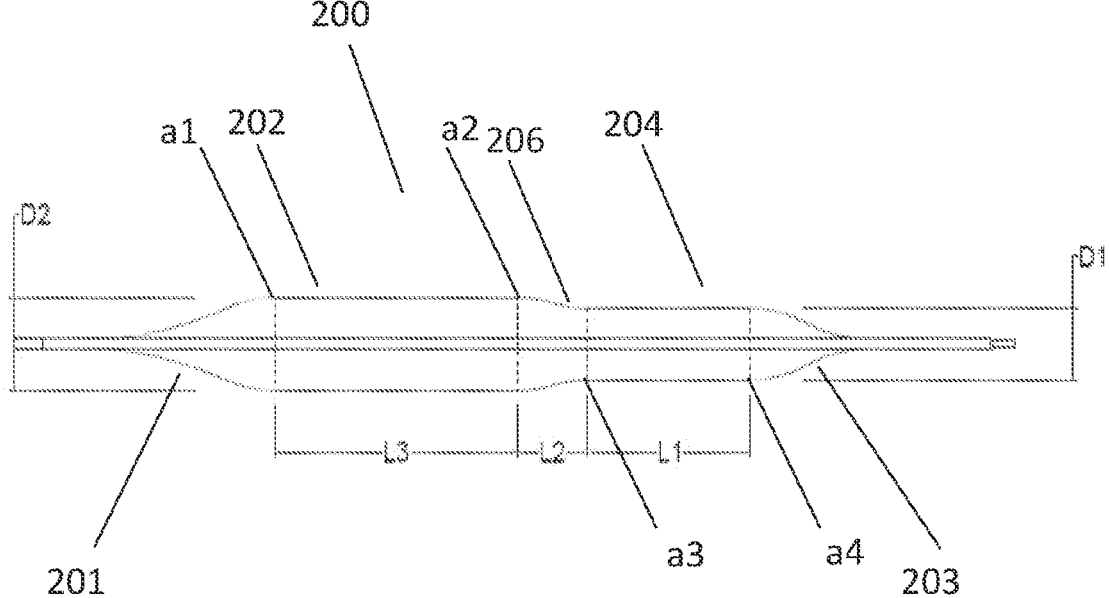
FIG. 3 represents a stepped balloon in accordance with an embodiment of the present invention.

As depicted in FIG. 3, the balloon 200 is a long and stepped percutaneous transluminal coronary angioplasty balloon which that is explicitly designed to suit the branching lesions of the parent main vessel which have smaller diameter. The purpose of the stepped balloon is to expand the stent 100 in the "bit by bit" manner so that it can complement physiology of the lesions in the main branch and the side branch of the artery.

The balloon 200 of the present invention may be made of one or more medical grade polymers which include, without limitation, polyamide (nylon 6, nylon 12, etc.), pebax, polyurethane, etc. In an embodiment, the balloon 200 is made of polyamide i.e. nylon 12. The use of nylon 12 for preparation of the balloon 200 offers excellent abrasion resistance and provides a smooth surface to the balloon 200.

In an embodiment, the balloon 200 may be manufactured using a polyamide tubing as described in FIG. 2 below. The rated burst pressure of the balloon 200 is around 16 Bar and the actual burst pressure is ≥21 Bar.

As shown in FIG. 3, the balloon 200 includes a proximal end 201 and a distal end 203. The balloon 200 extends between the proximal end 201 and the distal end 203. The double wall thickness at the proximal end 201 is around 0.043 mm to 0.052 mm with a considerable variation of +0.010 mm and −0.0050 mm. The double wall thickness at the distal end 203 is around 0.052 mm to 0.058 mm with the considerable variation same as the proximal end 201.

The balloon 200 is provided with a proximal zone 202 and a distal zone 204, separated by a transition zone 206. In an embodiment, the proximal zone 202 has a greater inflated diameter than the distal zone 204. Alternatively, the relative dimensions may be reversed, such that the distal zone 204 has a greater inflated diameter than the proximal zone 202, such as for use in a retrograde catheterization from the branch vessel into the main vessel.

The diameters and lengths of the proximal zone 202 and distal zone 204 may be varied, depending upon the intended target site. The proximal zone 202 may be provided with an inflated diameter in a range of 2.00 mm to 6.00 mm, and the distal zone 204 may have an inflated diameter in a range of 1.00 mm to 5.00 mm. In an embodiment, the proximal zone 202 has an inflated diameter of 3.00 mm to 4.00 mm and the distal zone 204 has the inflated diameter of 2.00 mm to 4.00 mm with deviation of ±0.15 mm. In general, the inflated diameter of the proximal zone 202 is at least 1% of the inflated diameter of the distal zone 204.

The proximal zone 202 has a working length defined as the axial length between a proximal shoulder a1 and a distal shoulder a2. The working length of the proximal zone 202 may be in a range of 4.00 mm to 8.00 mm. In an embodiment, the working length of the proximal zone 202 is in a range of 5 mm to 7 mm. The working length of the distal zone 204 extends from a proximal shoulder a3 to a distal shoulder a4. The working length of the distal zone 204 may be in a range of 5 mm to 20 mm. In one embodiment, the working length of the distal zone 204 is in range of 6 mm to 19 mm. In the illustrated embodiment, each of the proximal zone 202 and the distal zone 204 has a cylindrical inflated profile. However, noncylindrical configurations may also be utilized, depending upon the desired clinical result.

Figure 5:
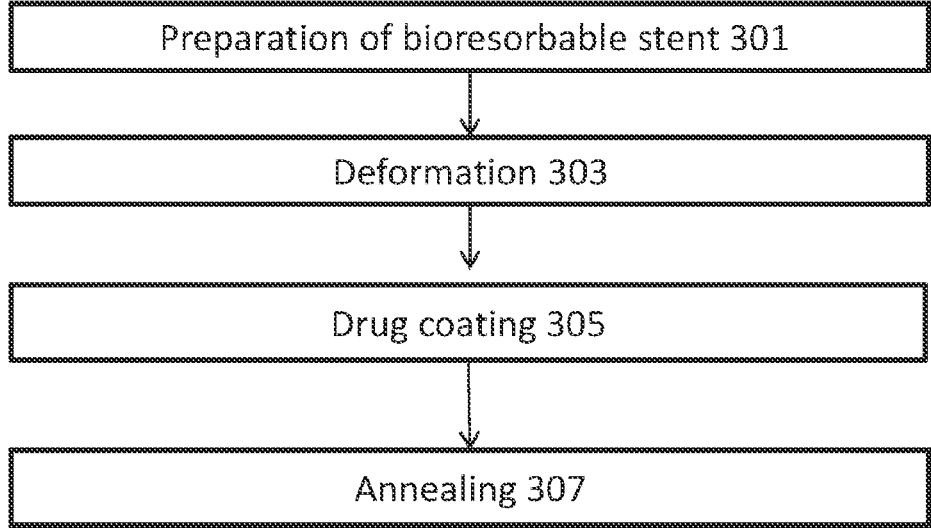
FIG. 5 represents a flow chart depicting a process involved in manufacturing of the balloon in accordance with an embodiment of the present invention.

FIG. 5 represents the steps for fabrication of the balloon 200 using a polyamide tubing. At step 301, the polyamide tubing is subjected to a parison forming process using a double end stretcher machine to yield a parison tube. Various parameters such as temperature and pressure may be maintained for axially stretching the tubing from both ends during the aforesaid process. The temperature for the given process may range between 140° C. and 170° C., preferably 145° C. to 165° C. and pressure may range between 2.0 bar to 6.0 bar, preferably 3.5 bar to 5.0 bar. The polymer tubing may include an outer diameter and an inner diameter, in a range of 1.0 mm to 1.25 mm and 0.63 mm to 0.79 mm respectively depending on the desired dimensions of the balloon 200.

Figure 5A:
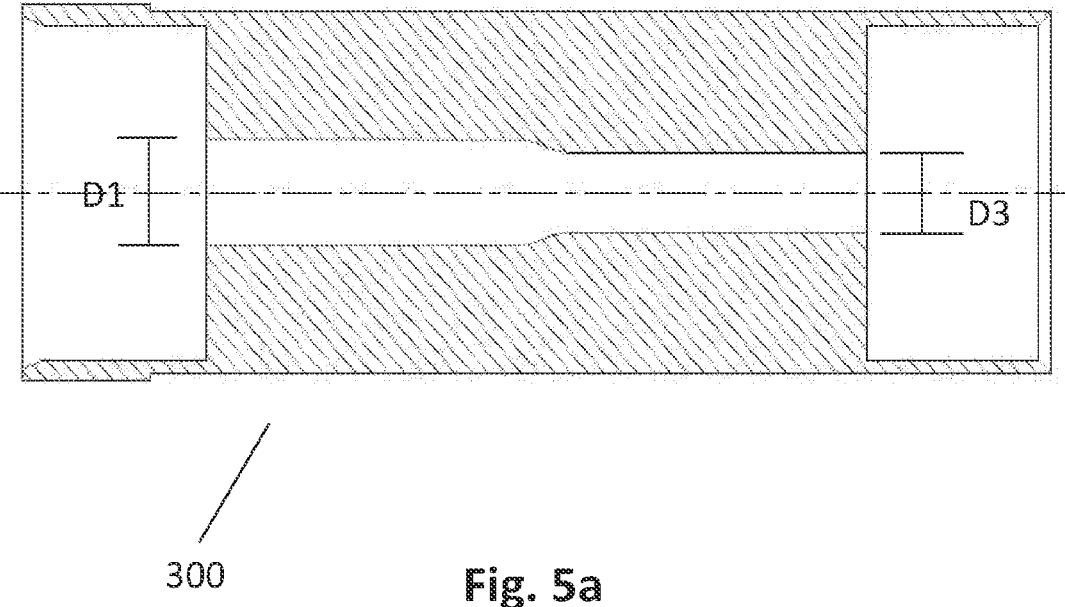
FIG. 5*a* represents a mold used to manufacture the stepped balloon in accordance with an embodiment of the present invention.

Post parison forming, at step 303, the parison tube is subjected to a process of stretch blow molding using a pre-defined mold 300 as shown in FIG. 5a. The mold 300 may be made up of any metal known in the art that can withstand high temperatures and pressures during the stretch blow molding process. The mold 300 may be made of material such as without limitation, steels, wrought aluminum alloys, copper alloys etc. In an embodiment, the mold 300 is made of beryllium copper. The mold 300 includes seamless inner surface with stepping edges to obtain the stepped balloon after stretch blow molding process.

In an embodiment, the stretch blow molding is executed in two phases. In the first phase, the parison tube is subjected to a temperature ranging between 55° C. to 75° C., preferably 60° C. to 70° C. and the medical grade nitrogen gas pressure is maintained between 20 bar to 40 bar, preferably 25 to 35 bar.

In the second phase, the temperature of the first phase is maintained while the nitrogen gas pressure is reduced and set between 10 bar to 40 bar, preferably 15 bar to 30 bar.

Subsequently, at step 305, the molded tube is subjected to a heat setting process in order to enhance the shape memory of the balloon 200. The temperature range at the time of heat setting process may be between 125° and 145° C. The mold is then subjected to immediate cooling by subjecting it to a temperature ranging between 15° and 25° C. to obtain a stepped balloon.

The stepped balloon may then be subjected to an annealing process at step 307. The process of annealing may be performed by a known process as disclosed in Indian patent application number IN201921047822.

Figure 6:
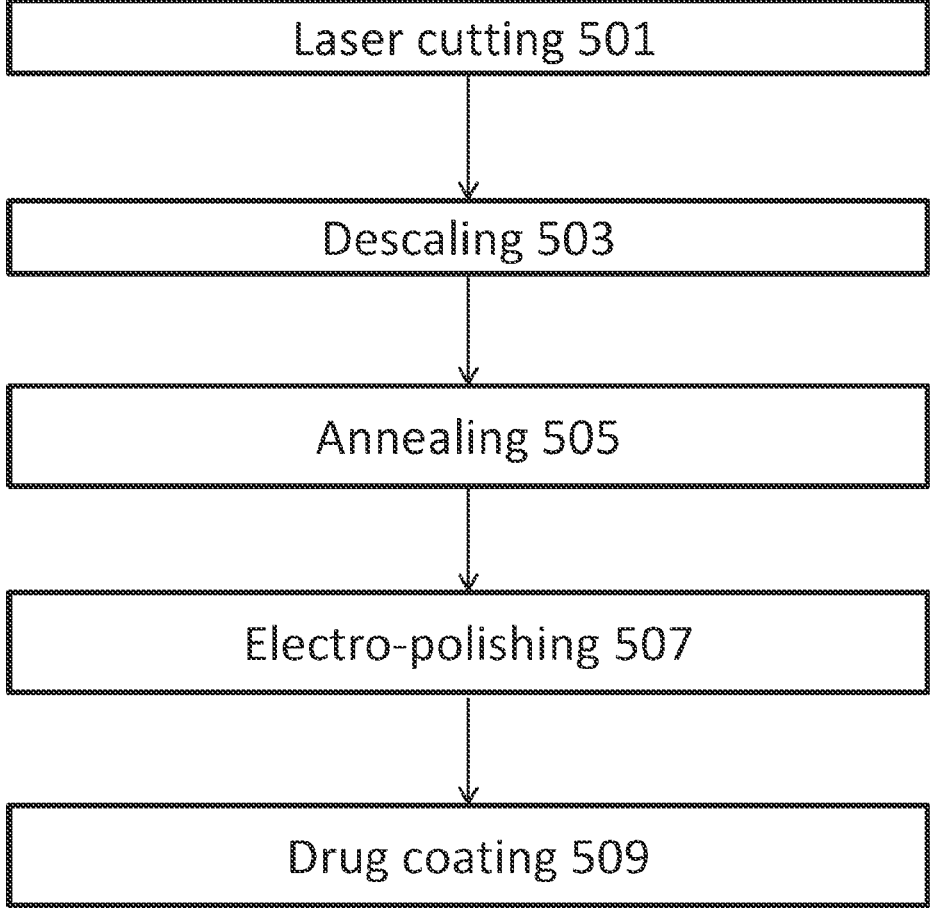
FIG. 6 represents a flow chart depicting a process involved in manufacturing of the stent in accordance with an embodiment of the present invention.

FIG. 6 represents a flow chart depicting a process involved in manufacturing of the stent 100 (depicted in FIG. 2).

In an embodiment, a cobalt chromium tube is used for manufacturing the stent 100. The diameter and wall thickness of the tube may be varied depending upon the desired characteristics of the stent 100 such as radial strength, flexibility, holding capacity, etc.

At step 501, the cobalt chromium tube of desired diameter is laser cut in a pre-defined configuration to obtain a laser cut tube. Alternately, other processes may also be followed to fabricate the stent 100.

Laser cutting of the cobalt chromium tube is conducted by a known process as disclosed in Indian patent application number IN201921047822.

Post laser cutting, the laser cut tube is subjected to descaling process to form a descaled stent at step 503. The laser cut tube may be dipped in a descaling solution for removing the burrs and/or particles from the surface of the laser cut tube. The descaling solution used for the above purpose may be one of, purified water, nitric acid, hydrofluoric acid, sodium tetrafluoro borate, etc.

At step 505, the descaled stent may be annealed to remove hardness, increase ductility and to eliminate internal stress in the stent 100 to form an annealed stent. The annealed stent may be further subjected to electro-polishing process for removal of oxide layer formed over the descaled stent at step 507. Further, electro-polishing highly improves the finish of metallic stent 100. It is used to polish, passivate, and deburr metal parts from the surface of stent. The process of electro-polishing stent utilizes ethylene glycol solution.

The stent 100 formed from the above process has a uniform diameter in the range of 1 mm to 2 mm. In an embodiment, the diameter of the stent 100 is 1.8 mm. The thickness of the struts of the stent 100 may range from 40 micron and 100 microns, preferably 45 microns to 65 microns.

Optionally/additionally, the stent 100 obtained at step 507, may be drug coated at step 509. The stent may be coated with an anti-proliferative drug or a formulation of anti-proliferative drug as well as a polymer or multiple polymers. Such a coating may be executed by any method known in the art, such as spray coating, spin coating, electro-spin coating, rolling, painting, sputtering, vapor deposition, etc. The said coating may be performed on an inner surface, an outer surface or both surfaces of the stent 100. The anti-proliferative drug may be selected from one or more of, without limitation, sirolimus, biolimus, zotarolimus, everolimus or the like from the -limus family of drugs. The polymer may acts as an excipient and may be selected from one or more of poly-I-lactic acid (PLA) and poly (lactic-co-glycolic acid) (PLGA), poly-DL-lactic acid (PDLLA) and poly(I-lactide-co-ε-caprolactone) (PLEC) etc.

In an embodiment, a formulation of the anti-proliferative drug includes sirolimus and a mixture of poly DL-lactide co-glycolide and poly L-lactide. The formulation may include a drug polymer ratio of 35:65. Such a formulation may be prepared in any solvent known in the art such as without limitation, methylene chloride, chloroform, acetone, methanol and mixtures thereof. In an embodiment, the formulation is coated on the outer surface of the stent 100 with a drug dose of approximately 1.25 μg/mm2 of the stent surface area.

The thickness of the coated layer may be less than 7 μm. In an embodiment, the thickness of the coating is between 2 μm and 3 μm. The drug coating on the stent 100 helps in preventing initial thrombosis after the implantation of stent 100.

The aforesaid invention is now described with the help of the following examples:

Example 1: A side branch stent 'A' having a total length (L) of 24 mm was implanted in bifurcated diffused long side branch lesions. The length (L3) of side branch segment was 13.00 mm and the thickness of struts was around 65 microns. The stent 'A' included nine circumferential rows connected with each other through three S links and six Y connectors in the side branch segment. The stent 'A' was coated with an anti-proliferative drug for reducing the risk of initial thrombosis and restenosis.

The stent 'A' was found to have enhanced flexibility and radial strength and resulted in recoil of around 1.6%. Due to such recoil, the stent 'A' was found to appose the lumen well. Further, the thickness of the struts was observed to accelerate the growth of endothelial layer thereby rendering faster healing. The stent 'A' also reduced vascular injury.

Example 2 (Prior Art): A side branch stent 'B' having a total length (L') of 18 mm was implanted in bifurcated diffused long side branch lesions. The length (L3') of side branch segment was 5.5 mm and the thickness of the struts was around 85 micron. The structure of the stent 'B' involved four circumferential out-of-phase zigzag hoops linked together by one straight connector.

The stent 'B' failed to cover the entire length of diffused side branch lesion which led to damage to the side branch coronary artery. The stent 'B' was found to have reduced flexibility with recoil of around 15%. The stent 'B' was found to take longer time to form the endothelial layer thereby conferring slower healing. The stent was found to be susceptible to initial thrombosis and restenosis.

The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

We claim:

1. A stent system (50) comprising:

a balloon catheter (200*a*) having a balloon (200), the balloon (200) having a proximal zone (202), a transition zone (206) and a distal zone (204), wherein the proximal zone (202), the transition zone (206) and the distal zone (204) include progressively decreasing diameters respectively; and a stent (100) of a pre-defined length having a main branch segment (10), a transition segment (20) and a side branch segment (30), the stent (100) including an expanded state and a crimped state, the stent (100) being mounted over the balloon (200) in the crimped state such that the main branch segment (10) is mounted over the proximal zone (202), the transition segment (20) is mounted over the transition zone (206) and the side branch segment (30) is mounted over the distal zone (204);

wherein, in the expanded state, the main branch segment (10), the transition segment (20) and the side branch segment (30) of the stent (100) correspond to the respective zones of the balloon (200);

wherein the transition segment (20) includes plural rows of elongated members (21) connected to each other, wherein the main branch segment (10) is connected to the transition segment (20) via a row of first connectors (13*a*) and a row of second connectors (13*b*), and wherein the first connectors (13*a*) include S links that are tilted in a predetermined direction and the second connectors (13*b*) include double S links.

2. The stent system (50) as claimed in claim 1 wherein the proximal zone (202) includes an inflated diameter in a range of 2.00 mm to 6.00 mm.

3. The stent system (50) as claimed in claim 1 wherein the distal zone (204) includes an inflated diameter in a range of 1.00 mm to 5.00 mm.

4. The stent system (50) as claimed in claim 1 wherein the pre-defined length of the stent (100) is in a range of 16 mm to 29 mm.

5. The stent system (50) as claimed in claim 1 wherein the main branch segment (10) includes a length in a range of 4.5 mm to 7 mm.

6. The stent system (50) as claimed in claim 1 wherein the side branch segment (30) includes a length in a range of 3 mm to 25 mm.

7. The stent system (50) as claimed in claim 1 wherein the proximal zone (202) has a working length in a range of 4.00 mm to 8.00 mm.

8. The stent system (50) as claimed in claim 1 wherein the distal zone (204) has a working length in a range of 5.00 mm to 20.00 mm.

9. The stent system (50) of claim 1 wherein the stent (100) is coated with one of an anti proliferative drug, or a formulation of the anti-proliferative drug and at least one polymer.

10. The stent system (50) of claim 1 wherein the stent system (50) has a guide-catheter compatibility of 6F.

* * * * *